US011622587B2

(12) United States Patent
Luplow

(10) Patent No.: US 11,622,587 B2
(45) Date of Patent: Apr. 11, 2023

(54) SELF-TENSIONING AND RELEASABLE GRIPPING GLOVES

(71) Applicant: Harley Luplow, Harbor Springs, MI (US)

(72) Inventor: Harley Luplow, Harbor Springs, MI (US)

( * ) Notice: Subject to any disclaimer, the term of this patent is extended or adjusted under 35 U.S.C. 154(b) by 261 days.

(21) Appl. No.: 16/851,488

(22) Filed: Apr. 17, 2020

(65) Prior Publication Data
US 2020/0329794 A1 Oct. 22, 2020

Related U.S. Application Data

(60) Provisional application No. 62/920,177, filed on Apr. 17, 2019.

(51) Int. Cl.
*A41D 19/015* (2006.01)
*A61F 5/01* (2006.01)
*A61H 1/02* (2006.01)

(52) U.S. Cl.
CPC . *A41D 19/01547* (2013.01); *A41D 19/01582* (2013.01); *A61F 5/0102* (2013.01); *A61H 1/0288* (2013.01); *A61F 2005/0139* (2013.01); *A61F 2005/0158* (2013.01); *A61H 2201/1481* (2013.01); *A61H 2205/065* (2013.01)

(58) Field of Classification Search
CPC ........ A41D 19/01547; A41D 19/01588; A41D 19/01582; A41D 19/01594; A41D 19/00; A41D 19/015; A41D 19/0055; A61F 5/013; A61F 5/37; A61F 5/01; A61F 5/0102; A61F 2005/0139; A61F 2005/0132; A61F 2005/0137; A61F 2002/5093; B25J 17/00; A61H 2201/165; A61H 2201/1481; A61H 2201/065
See application file for complete search history.

(56) References Cited

U.S. PATENT DOCUMENTS 5,538,488 A 7/1996 Villepigue
10,603,190 B2 3/2020 Mateus Dias Quinaz

FOREIGN PATENT DOCUMENTS

WO WO2013006178 A1 1/2013

*Primary Examiner* — Rachael E Bredefeld
*Assistant Examiner* — Brant T Bennett
(74) *Attorney, Agent, or Firm* — Loomis, Ewert, Parsley, Davis & Gotting P.C.; Mikhail Murshak

(57) ABSTRACT

A releasable gripping glove is provided having one or more flexible artificial tendons extending through a finger section of a glove body. The flexible artificial tendon is configured to maintain a structurally articulated configuration when the finger section is articulated. Each tendon includes locking teeth that engages with a releasable locking tab extending form a locking mechanism configured to engage the locking teeth when the finger section is articulated. A release mechanism is provided to engage and disengage the locking mechanism. A thumb release rod is positioned within a thumb portion and connected to the release mechanism. The articulating of the finger section releasably locks the flexible artificial tendon in the articulated position, which is releasable through relaxing of the thumb portion.

14 Claims, 6 Drawing Sheets

SELF-TENSIONING AND RELEASABLE GRIPPING GLOVES

CROSS REFERENCE TO RELATED APPLICATION

Priority is claimed to U.S. Provisional Application No. 62/920,177 filed Apr. 17, 2019 which is incorporated herein by reference in its entirety.

FIELD

The present disclosure relates generally to gloves. More particularly, the present disclosure is directed to performance, sport, and work gloves for gripping to assist user safety and performance.

BACKGROUND

Hand weakness and fatigue occur when doing repetitive or stressful manual tasks. In a resort community it has been noticed that many recreational sailors complain of hand fatigue due to the constant demand to adjust the boat's sails and rigging. Other tasks and professions often require extended gripping and tension that is known to cause fatigue and reduced strength over time.

Some devices/systems are known to support in some of these situations. These may be simple systems, such as padded gloves, aiming at providing greater assistance and resistance to the hand. Others are more complex using electronic motors connected to artificial tendons attached to the fingers of a glove that offer push and pull capabilities. Motorized systems to pull and/or push artificial tendons or structures attached to the user's finger control the opening and closing range of the hand. Because of the cumbersome mechanical structures of these systems, often, they are costly, range of motion is severely limited, the gloves are bulky and heavy, and the presence of a motor is undesirable.

The use of a motor to move fingers has several drawbacks. the motor needs to be powered, typically with batteries, which not only involves a high energy consumption and the use of large batteries and/or low-powered motors but also prevents or limits the sport and everyday use of these systems; motors, typically more than one, turn systems more expensive. These systems are complex and bulky and are used to assist medical problems mainly in medical centers. Some use backpacks to integrate the components, are very expensive systems, and are also incompatible with the normal use of the hand. In practice, hand support systems are complex, cumbersome and add volume which prevents the normal use of the hand.

U.S. Pat. No. 5,538,488 to Villepigue provides for a glove for exercising digits of a human hand. The device includes an inner glove for receiving a human hand therewithin. Digit cups are secured to the inner glove for receiving the outermost portion of each digit. A plurality of spring-loaded tension cables extend along a posterior of the glove and operate to resist motion of the glove during closing of the hand. An adjustment assembly effects tensioning of the cables to a desired resistance.

WO/2013/006178 to Land et al. provides for a hand movement device or a "glove" for positioning about a hand of a user. The glove includes a first anchor element positioned about a base surface of the glove, a second anchor element positioned at a tip of a finger portion of the glove, and an active spring member positioned between the first and second anchor elements. The active spring member is fixedly secured to the first anchor element and movable through the second anchor element to thereby allow the spring member to bend about a joint of the finger when the finger is flexed. An activating element positioned adjacent the active spring member to heat or cool the active spring member thereby causing the spring member to bend or straighten is provided, and the glove includes an intermediary support device for housing the spring element and for connecting the first anchor element to the second anchor element.

U.S. Pat. No. 10,603,190 to Quinaz provides for joint assistive and locking device for assisting and locking joints. The device includes a supporting structure in the joint, at least one tensioning system fixed to the supporting structure and at least one artificial tendon connected to the tensioning system. The tension system interacts with the locking system in order to assist the user's joints when needed.

SUMMARY

The present disclosure provides for a releasable gripping glove including: (a) a flexible artificial tendon extending through a finger section of a glove body, the flexible artificial tendon extending from a distal end of the finger section to a central hub portion near a proximal end of the finger section, the flexible artificial tendon configured to maintain a structurally articulated configuration when the finger section is articulated, each flexible artificial tendon having a plurality of locking teeth; (b) a releasable locking tab extending from a locking mechanism configured to engage the locking teeth of the flexible artificial tendon when the finger section is articulated causing the plurality of locking teeth to ratchet forward and lock the flexible artificial tendon in the articulated configuration, the locking mechanism having a release shaft abutting the locking tab; (c) a release mechanism provided in the central hub portion engaging the release shaft of the locking mechanism; and (d) a thumb release rod positioned within a thumb portion connected to the release mechanism configured to extend the release shaft to disengage the locking feature from the locking teeth of the flexible artificial tendon when the thumb portion is relaxed. The articulating of the finger section releasably locks the flexible artificial tendon in the articulated position, which is releasable through relaxing of the thumb portion.

The present disclosure further provides for a releasable gripping glove that includes four independently articulating flexible artificial tendons, each having a plurality of locking teeth. Each flexible artificial tendon: (i) corresponds to each finger digit of a hand and extends through corresponding finger pockets of the glove body, and (ii) extends from the central hub potion and engages an independent corresponding locking mechanism having a locking tab and a release shaft abutting the locking tab. Each locking tab is configured to engage the locking teeth of the corresponding flexible artificial tendon when the finger sections are articulated causing the plurality of locking teeth of each flexible artificial tendon to ratchet forward and lock the flexible artificial tendons in an articulated configuration. The release mechanism engages each release shaft of each locking mechanism and is configured to extend each release shaft to disengage the locking tab from the locking teeth of each flexible artificial tendon when the thumb portion is relaxed.

In an example, the release mechanism includes a pair of side-by-side cam gears configured to rotate in response to the relaxing of the thumb portion thereby extending each of the release shafts to disengage the locking tabs from the locking teeth and each of the release shafts are anchored in one of the cam gears. At least one of the cam gears defines a cutout to receive the thumb rod configured to push against the cam gear causing the cam gears to rotate when the thumb portion is relaxed.

In another example, the release mechanism includes a series of twist rods configured to twist in response to the relaxing of the thumb portion thereby extending the release shafts to disengage the locking tabs from the locking teeth. The release shafts are connected to a release rod that is rotated at one end by an intermediate twist rod connected to first twist rod configured to receive the thumb rod configured push against the first twist rod causing it to rotate and initiating the twisting of the release rod to push against the release shafts when the thumb portion is relaxed.

The present disclosure provides for a releasable gripping glove including a flexible artificial tendon that is fabricated from a metal, plastic, or other material configured to hold an articulated shape to support a hand of a user in the articulated configuration. Additional strength and support can be achieved by anchoring the tendon at a fingertip position of the finger section.

In an example, a releasable sailing gripping glove is provided wherein the articulating configuration is configured to hold a line in a locked position and relieve stress on a user's hand.

The present disclosure provides for a method of supporting a hand grip that includes the steps of (a) providing releasable gripping glove as discussed above; (b) articulating the finger portion of the glove body; (c) ratcheting up the locking teeth of the locking mechanism; (d) locking the flexible artificial tendon in an articulated configuration to provide strength and support to a user; and (e) relaxing the thumb portion thereby releasing the locking mechanism to allow the flexible artificial tendons to unlock and release back. The method can further include four independent flexible artificial tendons corresponding to each finger of the glove body and configured to allow for independent finger movement and simultaneous release by the thumb portion.

For purposes of summarizing the disclosure, certain aspects, advantages, and novel features of the disclosure have been described herein. It is to be understood that not necessarily all such advantages may be achieved in accordance with any one embodiment of the disclosure. Thus, the disclosure may be embodied or carried out in a manner that achieves or optimizes one advantage or group of advantages as taught herein without necessarily achieving other advantages as may be taught or suggested herein. The features of the disclosure which are believed to be novel are particularly pointed out and distinctly claimed in the concluding portion of the specification. These and other features, aspects, and advantages of the present disclosure will become better understood with reference to the following drawings and detailed description.

BRIEF DESCRIPTION OF THE DRAWINGS

The figures which accompany the written portion of this specification illustrate embodiments and method(s) of use for the present disclosure constructed and operative according to the teachings of the present disclosure.

DETAILED DESCRIPTION

Referring to FIGS. 1-5, the present disclosure provides for a self-tensioning and releasable gripping glove 10. In contrast to existing products, the present disclosure provides for a glove 10 having no electronic components or at least no electrical components directed to cause assistance with gripping and maintaining an articulated position or configuration. The glove 10 of the present disclosure can be actuated by a user's hand H strength to close or articulate the fingers F of their hand to a desired position thereby locking the glove 10 in a supportive structural configuration and then trigger a grip release. In an example, the glove 10 is designed to assist user safety and performance and cover a broad array of uses from medical to sports to business and everyday life.

The gripping glove 10 of the present disclosure is configured to hold a user's grip from releasing until the user's thumb makes a backward or "relaxing" or "releasing" motion triggering the grip release. The ability to restrict a user's hand from releasing when the user relaxes the hand can be effective to assist anyone subject to hand stress and fatigue from gripping a variety of objects encountered in everyday life, sports and commercial activities. The releasable gripping glove 10 enables a user to quickly and repeatedly close and open a static grip position while allowing the user's hand to at least partially rest while grasping objects. Examples of suitable application for gripping assistance include but are not limited to carrying luggage, holding handlebars on bikes, pulling rigging on sailboats, holding a paint brush, running power equipment, moving boxes, furniture, heavy cargo, or otherwise, etc.

In an example, a glove 10 of the present disclosure can be effective as a sailing glove that would cinch the user's hand H around a line, yet let them relax their hand while their grip stayed tight on the line allowing them to leverage their arm and body strength, relieving some hand tension, when they pulled on the line. Once ready to release the line the user simply opens their hands, leading with the thumb, to trigger the grip release in preparation for the next tug on the sailing line. Other uses beyond sailing are also appropriate. Other examples include mountaineering gloves with metal fingertips or an additional wrist brace for added leverage.

In an example, a mechanical releasable gripping glove 10 is provided having a glove body 11. The glove body can form an inner glove defined by a liner 19A for receiving a hand H of a user. The glove body 11 further includes an outer glove 19B with mechanical components disposed therebetween the outer glove 19B and the inner glove 19A. In use, the user's hand H is physically separated from any mechanical components by the inner glove liner 19A.

Figure 1:
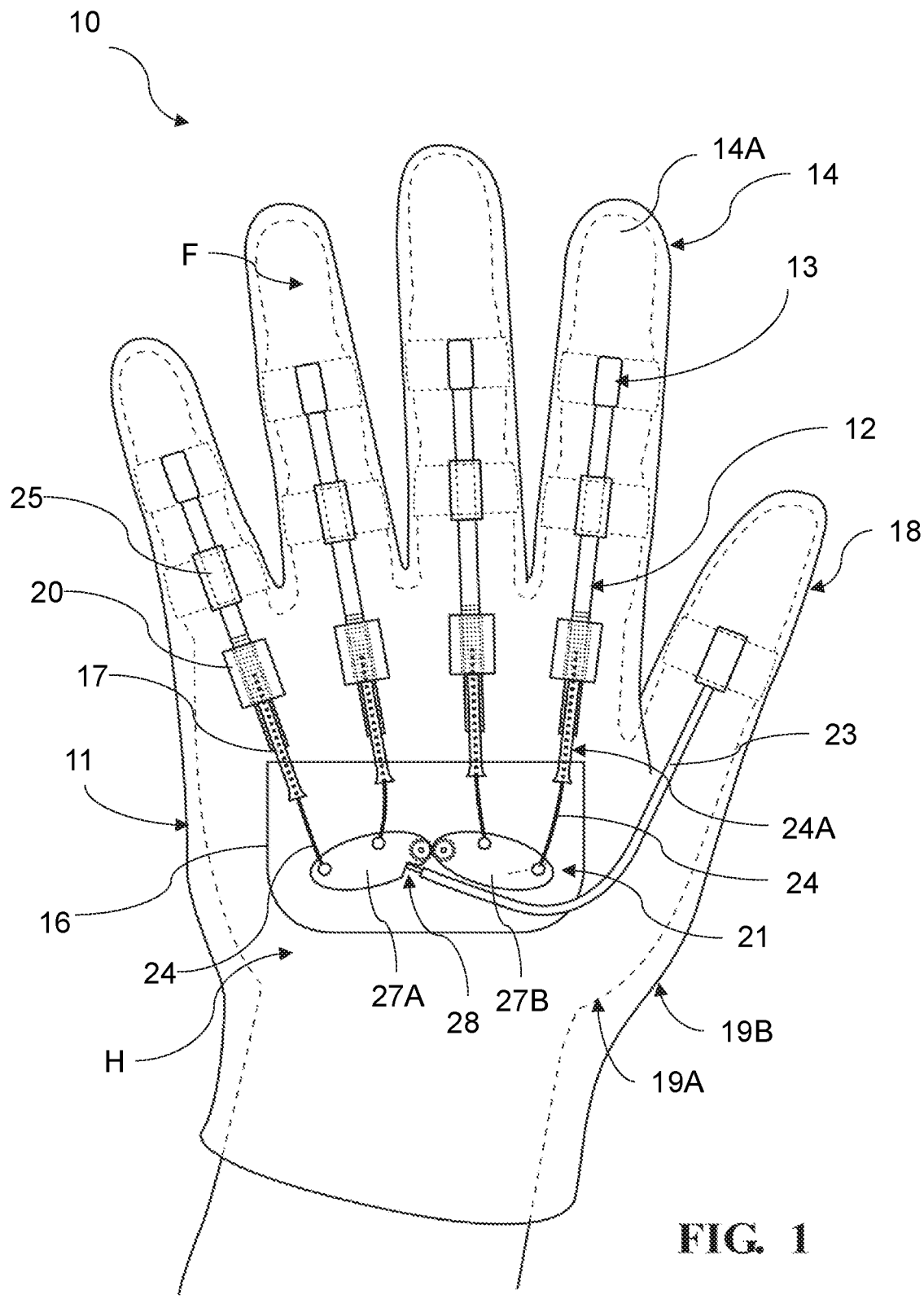
FIG. 1 illustrates a schematic of a releasable gripping glove of the present disclosure having a geared release mechanism.

Mounted in the glove body 11 and enclosed by the outer glove 19B is at least one flexible artificial tendon 12 that extends along a finger section 14. In the example of FIG. 1, four independent tendons 12 extend through each finger section 14 (can also be referred as a finger pocket or finger portion) of the glove body 11 from a proximal end near central hub 16 and extending up to an opposite distal end 13 anchored at a support ring portion 26. The proximal end of tendon 12 can be floating as it passes through a locking mechanism 20. Distal end 13, in this example, is positioned at between distal knuckles portions on glove body 11. In this example, the ring portion 26 extends along a side of the finger portion 14 at or near a fingertip section of the glove body 11 to prove structural support to the tendon 12. A proximal ring portion 26 is positioned between knuckles of the hand forming a channel for the tendon 12 to pass through to guide the tendon 12 and ensure it flexes and properly articulates with the user's finger. In this example the glove 10 is a closed finger glove, however, it is contemplated and within the scope of the present disclosure to include open finger designs having similar or identical mechanical structures that provide strength and structural support to a user during gripping. In another example, tendon 12 can be anchored at a fingertip section 14A of the finger portion 14.

When a user closes their gloved hand H by articulating their fingers F, the tendons 12 articulate with the fingers F allowing the user to grasp objects and the tendons 12 lock in place via an independent locking mechanism 20 engaging locking teeth 17 provided on each tendon 12. When the user relaxes their fingers F, the tendons 12 on four finger sections 14 remain locked and articulated at a desired grasping position (FIG. 2C) and will not move back as the tendon 12 is locked until the user releases a trigger with a backward or relaxing motion of the thumb portion 18. In a grasping locked position, the glove 10 can form an effective static hook shape that allows the user's natural "actual" grip to relax while their arm and body bear the weight of objects to be carried or pulled, thus relieving added stress on the hand or hands.

Figure 2A:
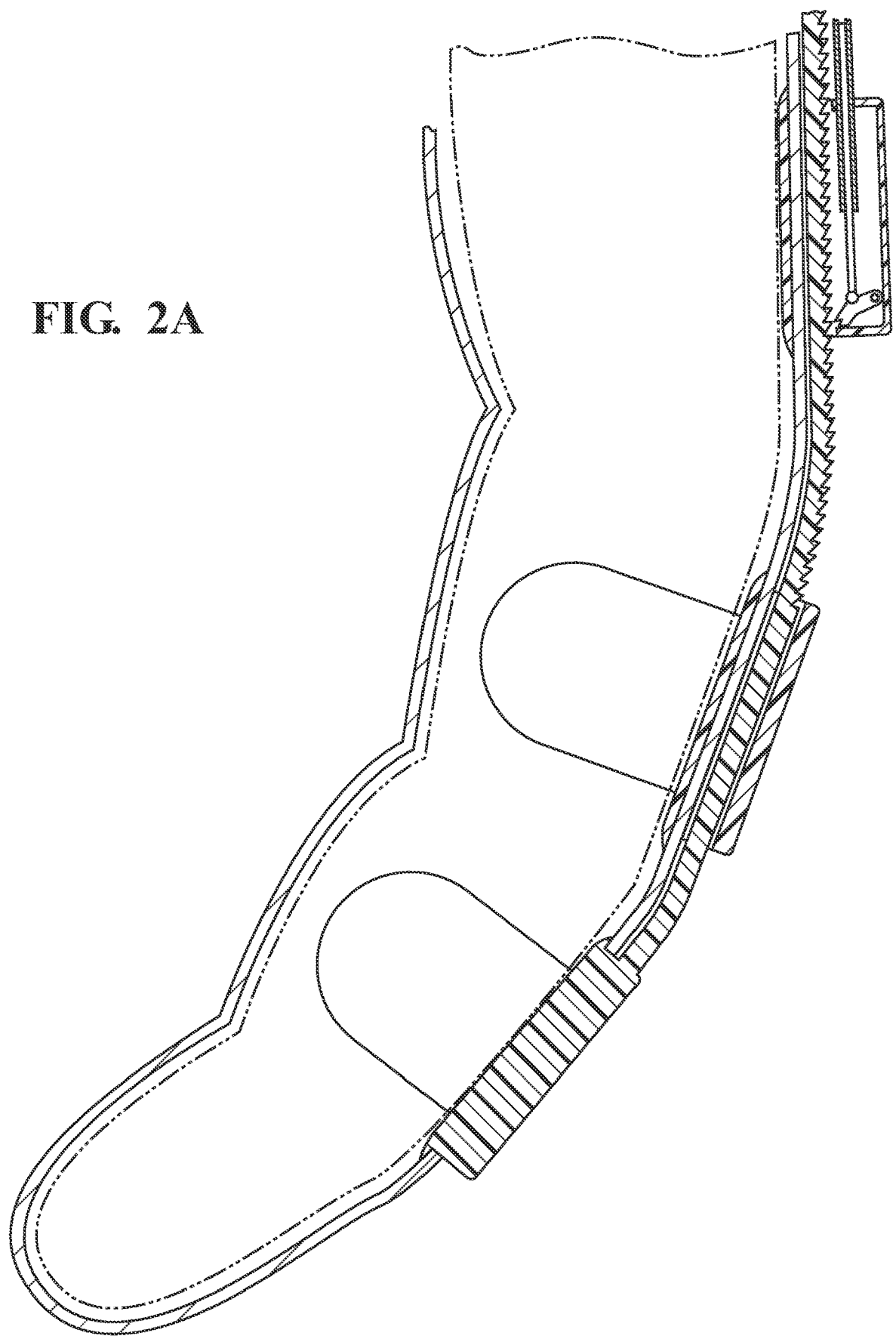
FIG. 2A illustrates a cross section of a finger portion of the releasable gripping glove with the locking mechanism disengaged.
Figure 2B:
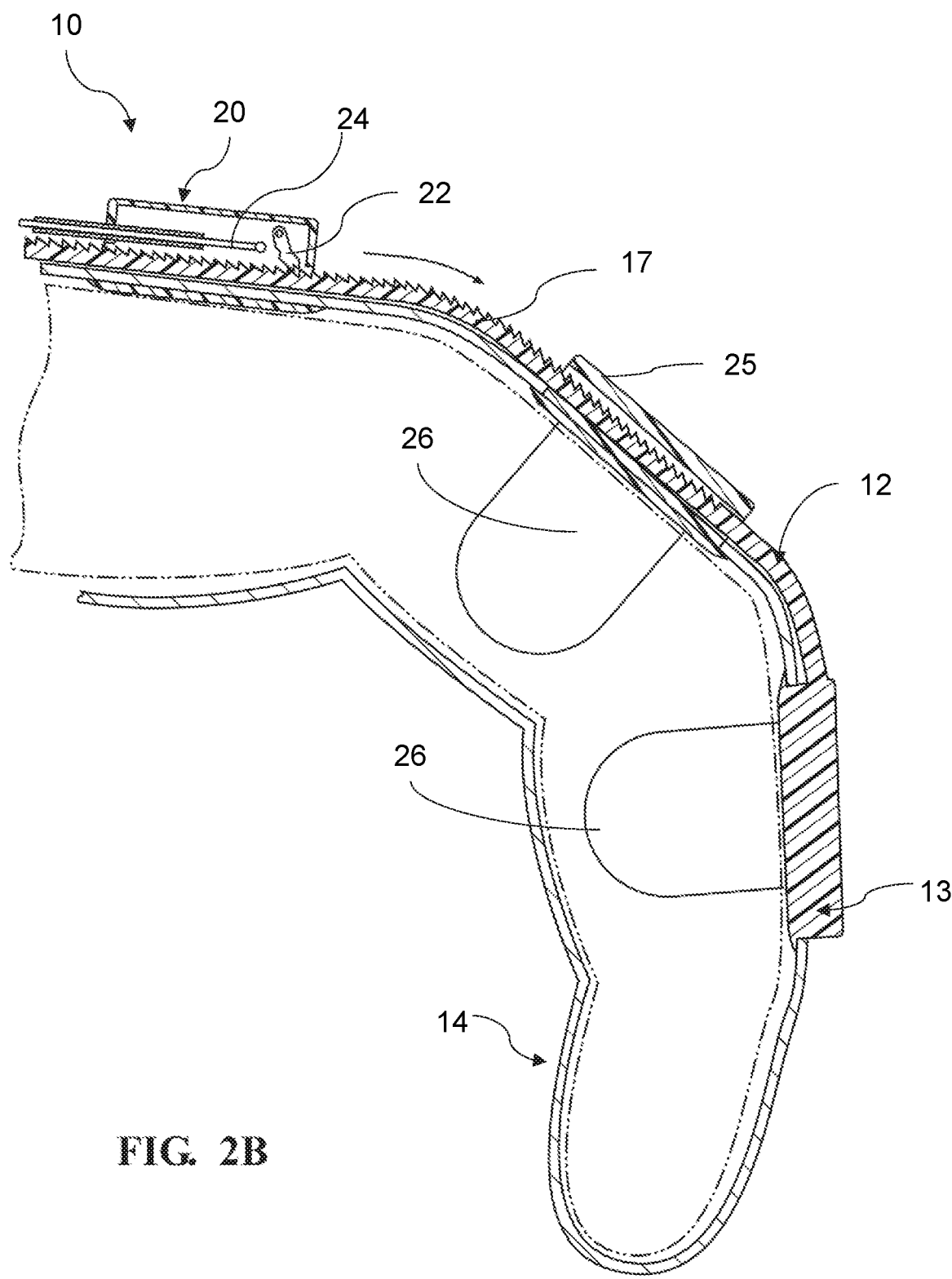
FIG. 2B illustrates a cross section of a finger portion of the releasable gripping glove in an articulated configuration with the locking mechanism initiated.
Figure 2C:
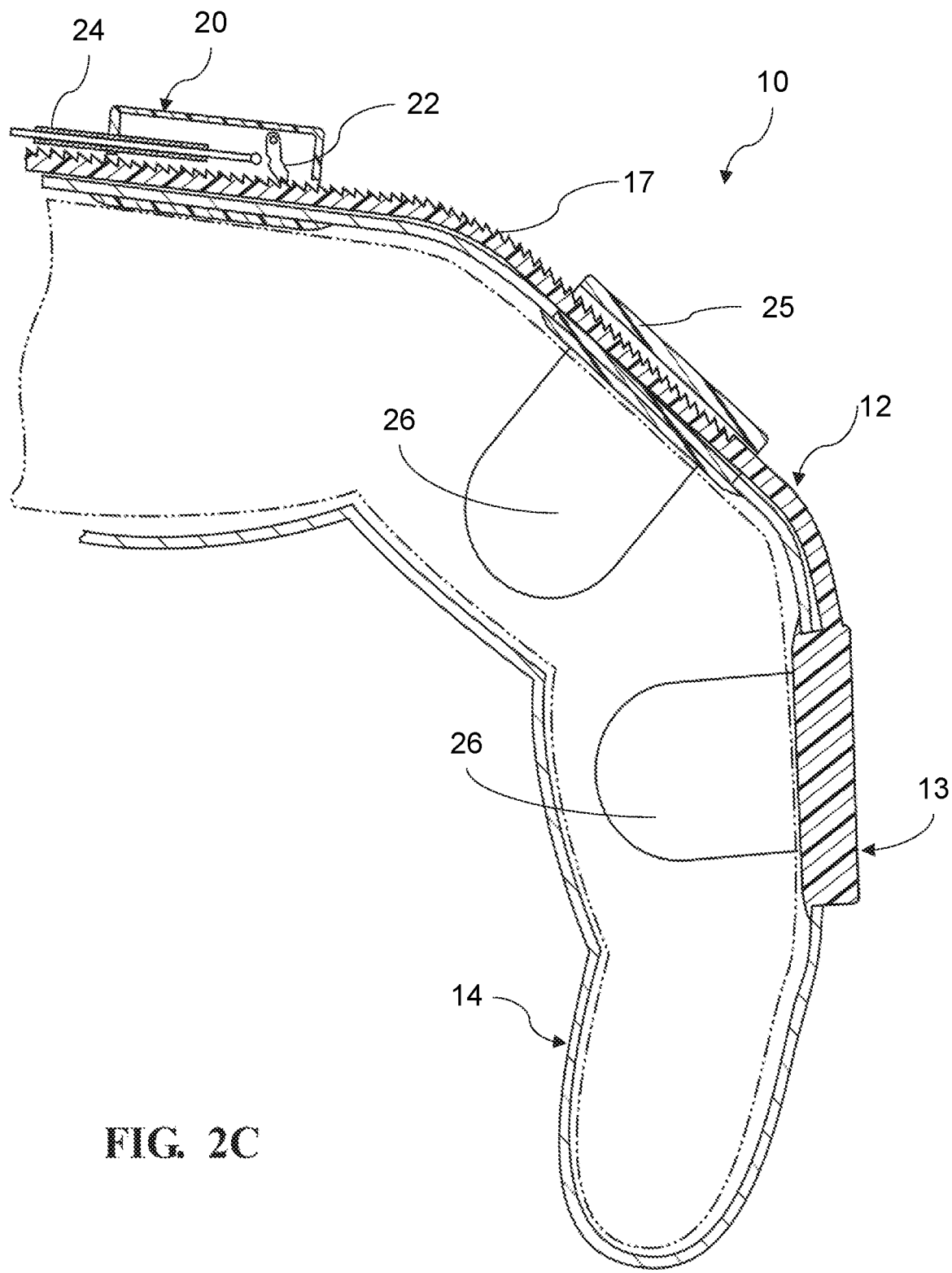
FIG. 2C illustrates a cross section of a finger portion of the releasable gripping glove in an articulated configuration with the locking mechanism engaged.
Figure 3:
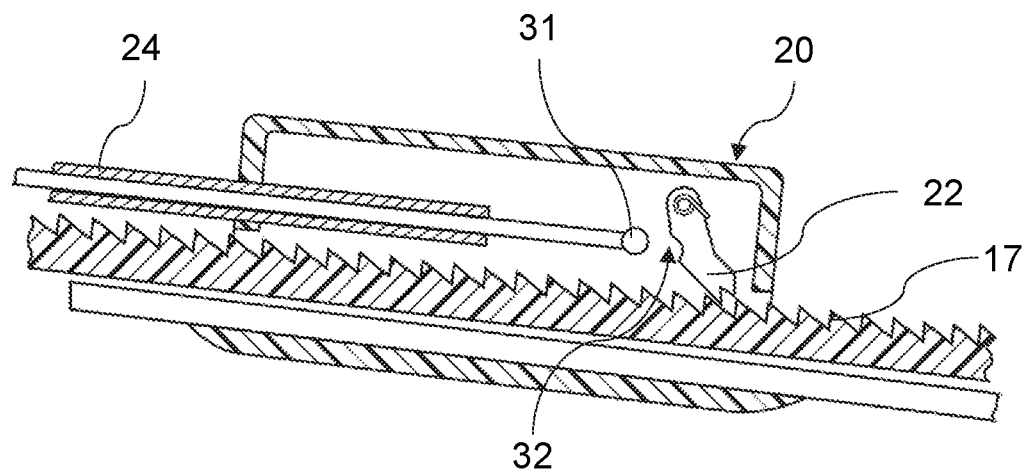
FIG. 3 illustrates a magnified schematic of the locking mechanism of the present disclosure.
Figure 4:
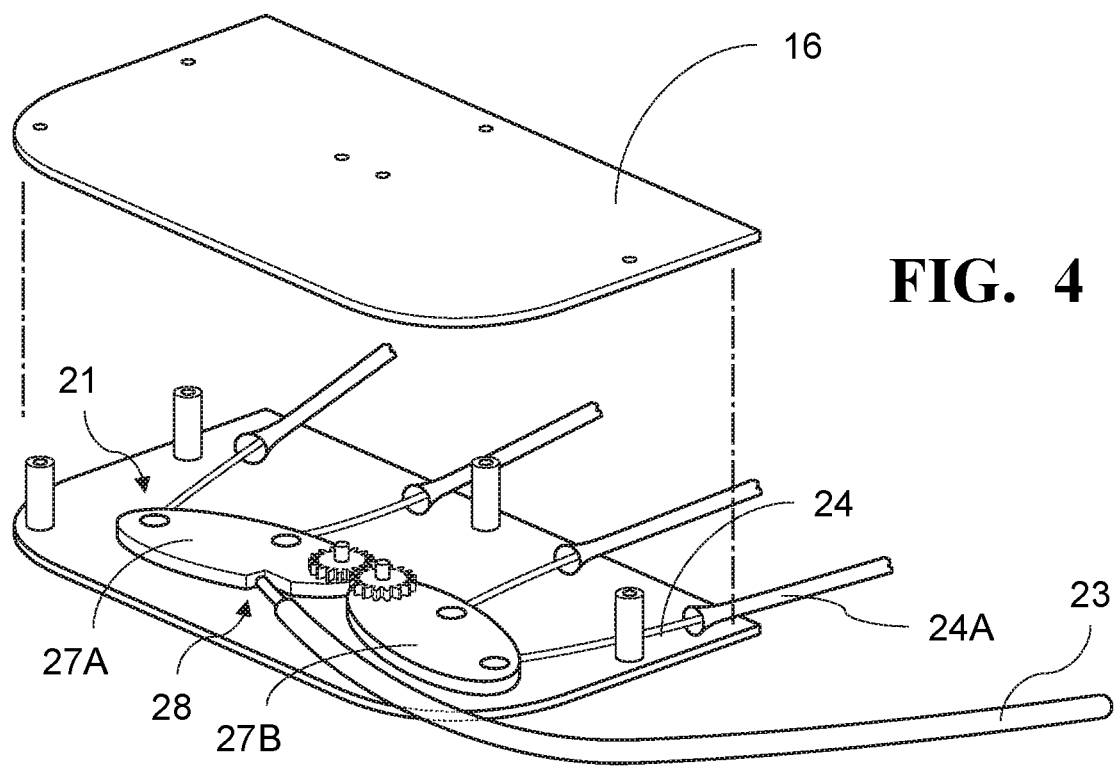
FIG. 4 illustrates an exploded view of a central hub portion of the release mechanism of FIG. 1.

The present disclosure provides a releasable gripping glove 10 that includes at least one flexible artificial tendon 12 extending through a finger section 14 of a glove body 11. The flexible artificial tendon 12 extends from a distal end 13 of the finger section 14 toward a central hub portion 16. The flexible artificial tendon 12 is configured to maintain a structurally articulated configuration when the finger section 14 is articulated (See FIG. 2C). Each tendon 12 includes a plurality of locking teeth 17. Glove 10 includes a releasable locking tab 22 that extends from a locking mechanism 20 configured to engage the locking teeth 17 of the flexible artificial tendon 12 when the finger section 14 is articulated (See FIGS. 2A-2B) causing the plurality of locking teeth 17 to ratchet forward (See FIG. 3) and lock the flexible artificial tendon 12 in the articulated configuration (FIG. 2C). The locking mechanism 20, in this example, includes a release shaft 24 abutting the locking tab 22. In this example, release shaft is provided within a sheath 24A to support and guide the release shaft 24 as it moves from a disengaged to an engaged position.

In this example, locking tab 22 defines a receiving cavity or cutout 32 for abutting against an end 31 of the release shaft 24. The receiving cutout 32 is sized and shaped to effectively receive end 31 of release shaft 24 such that the locking tab can be spring loaded to only rotate back during ratcheting and lock against the end 31 if the fingers F try to push back. This forms the locking portion of the locking mechanism 20 and thus allows the tendons 12 to remain in the articulated configuration of FIG. 2C. Locking tab 22 defines a mating groove or teeth that interact with the angled teeth 17 of the tendon 12. Accordingly, when the locking mechanism releases the tab 22 as shown in FIG. 2A, the locking teeth 17 no longer interact with tab 22 and thus can retract to an open configuration freely. In another example, the locking tab is prevented from rotating back towards the hand when the release shaft 24 engages the tab 22 and when the release mechanism 21 pulls release shaft 24 back, the tab 22 is free to rotate and disengage from teeth 17.

Glove 10 includes a release mechanism 21 provided in the central hub portion 16 engaging the release shaft 24 of the locking mechanism 20. A thumb release rod 23 is positioned within a thumb portion 18 and connected to the release mechanism 21. The release mechanism 21 is configured to extend the release shaft 24 to disengage the locking feature 20 from the locking teeth 17 of the flexible artificial tendon 12 when the thumb portion 18 is relaxed. The articulating of the finger section 14 releasably locks the flexible artificial tendon 12 in the articulated position which is releasable through relaxing of the thumb portion 18.

The glove body 11 can define an inner glove having a liner 19A forming a cavity for receiving a hand H and fingers F of a user. The glove body 11 defines an outer glove cover 19B forming an outer surface of the glove and enclosing the flexible artificial tendon 12, locking mechanism 20, release mechanism 21, central hub 16 and thumb release rod 23. In an example, the flexible artificial tendon 12 extends through a guide channel 25 configured to provide structural support during articulation.

In yet another example, the gripping glove 10 of the present disclosure further includes partial ring supports 26 positioned between each knuckle of a finger section 14, wherein a first ring support 26 extends along a side portion of the finger section 14 and anchors the flexible artificial tendon 12 near the distal end 13 of the finger section 14. In another example, the tendon 12 is anchored at a fingertip section 14A to provide additional range of motion, strength, and/or structural support.

In the example of FIG. 1, the releasable release mechanism 21 includes a pair of side-by-side cam gears 27A and 27B configured to rotate in response to the relaxing of the thumb portion 18 thereby extending the release shaft 24 to disengage the locking tab 22 from the locking teeth 17. At least one of the cam gears 27A defines a cutout 28 (See FIG. 4) to receive the thumb rod 23 configured push against the cam gear 27A causing the cam gears 27A and 27B to rotate when the thumb portion is relaxed to disengage the locking tab 22 through the release shaft 24. This releases the locking teeth 17 and allows the tendon 12 to move freely from an articulated (i.e., gripped) position to a relaxed or unflexed position.

Figure 5:
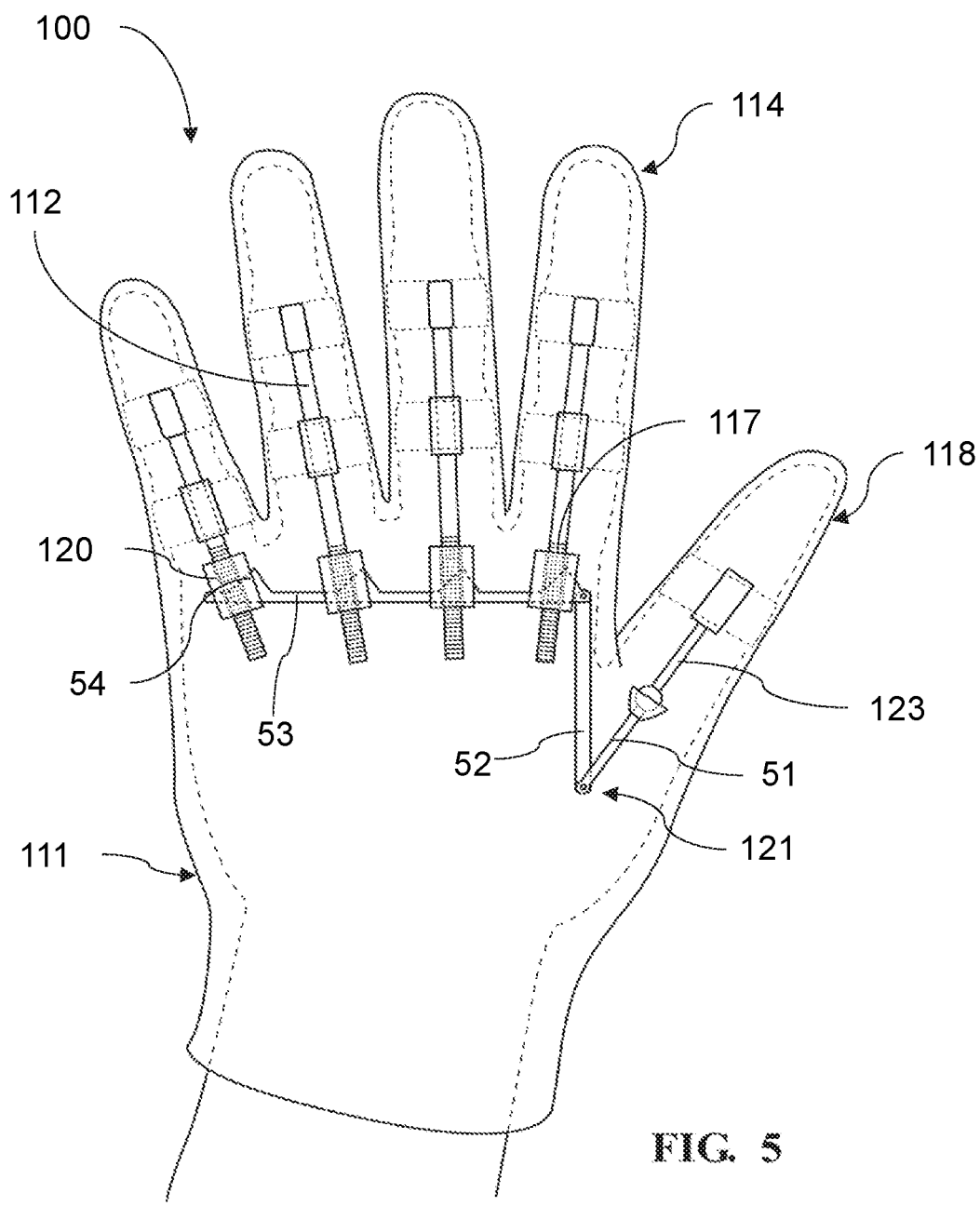
FIG. 5 illustrates a schematic of a releasable gripping glove of the present disclosure having a twist rod release mechanism.

In the example of FIG. 5, the releasable gripping glove 100 includes a release mechanism 121 including a series of twist rods 51 and 52 configured to twist in response to the relaxing of the thumb portion 118 thereby extending the disengaging locking mechanism 120 from the locking teeth 117. In this example, locking mechanism 120 includes a release rod 53 that rotates and serves a dual function of engaging and disengaging the locking teeth 117. Release rod 53 defines a locking tab 54 that engages the locking teeth 117. In this example, four locking tab 54 are provided extending from a single rod 53, each of which are configured to engage or disengage the locking teeth 117 of their respective tendon 112. Release rod 53 is engaged by the release mechanism 121 and can be rotated at one end by an intermediate twist rod 52. Intermediate twist rod 52 is connected to first twist rod 51 configured to receive the thumb rod 123 which configured push against the first twist rod 51 causing it to rotate and initiating the twisting of the release rod 53 to release the locking teeth 117 and allows the tendon 112 to move freely when the thumb portion 118 is relaxed. In this example, the release rod 53 includes at least four push tabs 54 that rotate, serving as an alternative design to the earlier mentioned releasable locking tab 22 and such rod 53 releases the locking teeth 117 to disengage the locking mechanism 120.

FIGS. 1 and 5 illustrate four independently articulating flexible artificial tendons 12 and 112, each having a plurality of locking teeth 17 and 117 respectively. Each flexible artificial tendon 12/112: (i) corresponds to each finger digit F of a hand H and extends through corresponding finger pockets or finger sections 14/114 of the glove body 11/111, and (ii) engages an independent corresponding locking mechanism 20/120. For locking mechanism 20, a locking tab 22 engages with a release shaft 24 abutting the locking tab 22. Locking mechanism 120 includes a release rod 53 having a plurality of locking tabs 54. Each locking tab 22/54 is configured to engage the locking teeth 17/117 of the corresponding flexible artificial tendon 12/112 when the finger sections 14/114 are articulated causing the plurality of locking teeth 17/117 of each flexible artificial tendon 12/112 to ratchet forward and lock the flexible artificial tendons 12/112 in an articulated configuration. The release mechanism 21/121 engages the release shaft 22 or the release shaft 53 of each locking mechanism 20/120, respectively. The release mechanism 21/121 is configured to extend each release shaft 24 to disengage the locking tab 22 from the locking teeth 17 of each flexible artificial tendon 12 or rotate release rod 53 to disengage the locking mechanism 120 when the thumb portion 18/118 is relaxed, respectively. The release mechanism 21 includes the pair of side-by-side cam gears 27A and 27B configured to rotate in response to the relaxing of the thumb portion 18 thereby extending each of the release shafts 24 to disengage the locking tabs 22 from the locking teeth 17. Each of the release shafts 24 are anchored in one of the cam gears 27A or 27B. In the example of FIG. 1, each cam gear 27A and 27 B anchors two release shafts. The twist rod example of FIG. 5 also operates to simultaneously release each of the independent locking mechanisms 120 of each finger section 114.

The present disclosure provides for a flexible artificial tendon that is fabricated from a metal configured to hold an articulated shape to support a hand of a user in the articulated configuration. In another example, the tendons are fabricated from a suitably strong plastic or composite material able to be flexed easily but still retain its shape in a locked configuration.

The present disclosure further provides for a method of use of the glove 10 that includes articulating the finger sections 14 of the glove body 11 and causing the locking mechanism 20 to lock the tendons 12 in an articulated configuration during gripping. To release, the thumb portion 18 is relaxed backwards actuating the release mechanism 21.

It should be noted that the steps described in the method of use can be carried out in many different orders according to user preference. The use of "step of" should not be interpreted as "step for", in the claims herein and is not intended to invoke the provisions of 35 U.S.C. § 112(f). Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the disclosure described herein are exemplary and numerous modifications, variations and rearrangements can be readily envisioned to achieve substantially equivalent results, all of which are intended to be embraced within the spirit and scope of the disclosure. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A releasable gripping glove comprising:
    (a) at least one flexible artificial tendon extending through at least one finger section of a glove body, the at least one flexible artificial tendon extending from a distal end of the at least one finger section toward a central hub portion near a proximal end of the at least one finger section, the at least one flexible artificial tendon configured to maintain a structurally articulated configuration when the at least one finger section is articulated, the at least one flexible artificial tendon having a plurality of locking teeth;
    (b) a releasable locking tab extending from a locking mechanism configured to engage the locking teeth of the at least one flexible artificial tendon when the at least one finger section is articulated causing the plurality of locking teeth to ratchet forward and lock the at least one flexible artificial tendon in the articulated configuration;
    (c) a release mechanism provided in the central hub portion engaging the locking teeth; and
    (d) a thumb release rod positioned within a thumb portion connected to the release mechanism configured to disengage the locking tab from the locking teeth of the at least one flexible artificial tendon when the thumb portion is relaxed;
    wherein the articulating of the at least one finger section releasably locks the flexible artificial tendon in the articulated position, which is releasable through relaxing of the thumb portion,
    wherein the locking mechanism includes a release shaft abutting the locking tab configured to disengage the locking tab from the locking teeth, and the release mechanism includes a pair of side-by-side cam gears configured to rotate in response to the relaxing of the thumb portion thereby extending the release shaft to disengage the locking tab from the locking teeth.

2. The releasable gripping glove of claim 1, wherein the glove body defines an inner glove having a liner forming a cavity for receiving a hand and fingers of a user, and wherein the glove body defines an outer glove cover forming an outer surface of the glove and enclosing the at least one flexible artificial tendon, locking mechanism, release mechanism, central hub and thumb release rod.

3. The releasable gripping glove of claim 1, wherein the release mechanism is configured to extend the release shaft to disengage the locking tab from the locking teeth of the at least one flexible artificial tendon when the thumb portion is relaxed.

4. The releasable gripping glove of claim 1, wherein at least one of the pair of side-by-side cam gears defines a cutout to receive the thumb rod configured push against the cam gear defining the cutout causing the pair of side-by-side cam gears to rotate when the thumb portion is relaxed.

5. The releasable gripping glove of claim 1, wherein the at least one flexible artificial tendon is floating at a proximal end and extends through a guide channel configured to provide structural support during articulation.

6. The releasable gripping glove of claim 1, further comprising at least one partial ring support positioned between each knuckle of the at least one finger section, wherein a first ring support extends along a side portion of the at least one finger section and anchors the at least one flexible artificial tendon near the distal end of the at least one finger section.

7. The releasable gripping glove of claim 1, further comprising a plurality of independently articulating flexible artificial tendons, each having a plurality of locking teeth,
wherein each of the plurality of independently articulating flexible artificial tendons: (i) corresponds to a corresponding finger digit of a hand and extends through corresponding finger pockets of the glove body, and (ii) extends from the central hub portion and engages an independent corresponding locking mechanism having a locking tab,
wherein each locking tab is configured to engage the locking teeth of the corresponding flexible artificial tendon when the finger sections are articulated causing the plurality of locking teeth of each flexible artificial tendon to ratchet forward and lock the flexible artificial tendons in an articulated configuration,
wherein the release mechanism engages each locking mechanism and is configured to disengage the locking tab from the locking teeth of each flexible artificial tendon when the thumb portion is relaxed.

8. The releasable gripping glove of claim 7, wherein each locking mechanism includes a release shaft abutting the locking tab configured to disengage the locking tab from the locking teeth, and wherein each of the release shafts are anchored in one of the side-by-side cam gears.

9. The releasable gripping glove of claim 8, wherein at least one of the pair of side-by-side cam gears defines a cutout to receive the thumb rod configured to push against the cam gear defining the cutout causing the pair of side-by-side cam gears to rotate when the thumb portion is relaxed.

10. The releasable gripping glove of claim 1, wherein the at least one flexible artificial tendon is fabricated from a metal, a plastic, or composite configured to hold an articulated shape to support a hand of a user in the articulated configuration.

11. The releasable gripping glove of claim 1, wherein the gripping glove is a sailing glove configured for sailing and the articulating configuration is configured to hold a line in a locked position and relieve stress on a user's hand.

12. A method of supporting a hand grip comprising the steps of:
(a) providing releasable gripping glove according to claim 1;
(b) articulating the at least one finger portion of the glove body;
(c) ratcheting up the locking teeth of the locking mechanism;
(d) locking the at least one flexible artificial tendon in an articulated configuration to provide strength and support to a user;
(e) relaxing the thumb portion thereby releasing the locking mechanism to allow the at least one flexible artificial tendons to unlock and release back.

13. The method of claim 5, further comprising a plurality of independent flexible artificial tendons corresponding to each finger of the glove body and configured to allow for independent finger movement and simultaneous release by the thumb portion.

14. The releasable gripping glove of claim 7, wherein the plurality of independently articulating flexible artificial tendons includes four independently articulated flexible tendons.

* * * * *